US011963669B2

(12) United States Patent
Kramer et al.

(10) Patent No.: US 11,963,669 B2
(45) Date of Patent: Apr. 23, 2024

(54) REPROCESSING CASE

(71) Applicant: ASP GLOBAL MANUFACTURING GMBH, Schaffhausen (CH)

(72) Inventors: Kenneth S. Kramer, Trabuco Canyon, CA (US); Samuel J. Rhodes, Los Angeles, CA (US)

(73) Assignee: ASP Global Manufacturing GMBH (CH)

( * ) Notice: Subject to any disclaimer, the term of this patent is extended or adjusted under 35 U.S.C. 154(b) by 644 days.

(21) Appl. No.: 16/716,745

(22) Filed: Dec. 17, 2019

(65) Prior Publication Data

US 2020/0187767 A1 Jun. 18, 2020

Related U.S. Application Data

(60) Provisional application No. 62/781,479, filed on Dec. 18, 2018.

(51) Int. Cl.
*A61B 1/12* (2006.01)
*A61L 2/22* (2006.01)
*A61L 2/26* (2006.01)

(52) U.S. Cl.
CPC .............. *A61B 1/121* (2013.01); *A61L 2/22* (2013.01); *A61L 2/26* (2013.01); *A61L 2202/24* (2013.01)

(58) Field of Classification Search
CPC .............................................. A61L 2202/122
See application file for complete search history.

(56) References Cited

U.S. PATENT DOCUMENTS

| 4,506,544 | A | 3/1985 | Shimizu |
| 4,748,003 | A * | 5/1988 | Riley .................. B65D 77/225 422/11 |
| 4,783,321 | A | 11/1988 | Spence |
| 4,948,566 | A | 8/1990 | Gabele et al. |
| 5,279,799 | A | 1/1994 | Moser |
| 5,288,467 | A | 2/1994 | Biermaier |
| 5,425,815 | A | 6/1995 | Parker et al. |
| 5,814,009 | A | 9/1998 | Wheatman |
| 5,858,305 | A | 1/1999 | Malchesky |
| 5,882,589 | A | 3/1999 | Mariotti |
| 6,209,591 | B1 | 4/2001 | Taggart |

(Continued)

FOREIGN PATENT DOCUMENTS

| CN | 101637767 A | 2/2010 |
| CN | 103118581 A | 5/2013 |

(Continued)

OTHER PUBLICATIONS

Translation of KR 20080062342 A, 2006.*

(Continued)

*Primary Examiner* — Kevin Joyner
*Assistant Examiner* — Changru Chen
(74) *Attorney, Agent, or Firm* — Lerner David LLP

(57) ABSTRACT

A reprocessing case may be used to assist in reprocessing an instrument, such as an endoscope in an automated reprocessor. The reprocessing case may include various features such that the case may include and be transitioned between a closed configuration, an open configuration, and a disinfection configuration. In particular the reprocessor may transition the case to a disinfection configuration during a reprocessing procedure.

17 Claims, 7 Drawing Sheets

(56) References Cited

U.S. PATENT DOCUMENTS

| | | | |
|---|---|---|---|
| 6,217,835 B1 | 4/2001 | Riley et al. | |
| 6,365,102 B1 | 4/2002 | Wu et al. | |
| 6,365,103 B1 | 4/2002 | Fournier | |
| 6,485,684 B1 | 11/2002 | Mapson et al. | |
| 6,800,245 B1 | 10/2004 | Erbe et al. | |
| 7,749,330 B2 | 7/2010 | Lin et al. | |
| 8,591,668 B2 | 11/2013 | Pieroni et al. | |
| 10,086,100 B1 * | 10/2018 | Mauzerall | A61L 2/06 |
| 2002/0001537 A1 | 1/2002 | Hlebovy et al. | |
| 2002/0045328 A1 | 4/2002 | Kobayashi | |
| 2002/0098139 A1 | 7/2002 | Sparks | |
| 2004/0062692 A1 | 4/2004 | Lin et al. | |
| 2004/0105780 A1 | 6/2004 | Lin et al. | |
| 2004/0118413 A1 | 6/2004 | Williams et al. | |
| 2004/0134520 A1 | 7/2004 | Weber | |
| 2005/0025686 A1 | 2/2005 | Sargent et al. | |
| 2005/0042130 A1 | 2/2005 | Lin et al. | |
| 2005/0163655 A1 | 7/2005 | Lin et al. | |
| 2007/0207074 A1 * | 9/2007 | Jethrow | A61L 2/24 422/292 |
| 2008/0236621 A1 | 10/2008 | Lin et al. | |
| 2008/0240979 A1 | 10/2008 | Lin et al. | |
| 2017/0203014 A1 | 7/2017 | Kenley | |

FOREIGN PATENT DOCUMENTS

| | | | |
|---|---|---|---|
| CN | 104717934 A | 6/2015 | |
| DE | 36 32 675 A1 | 4/1988 | |
| JP | 2002325719 A | 11/2002 | |
| KR | 20080062342 A * | 12/2006 | H01L 21/67017 |
| WO | 93/17727 | 9/1993 | |
| WO | 2013/046010 A1 | 4/2013 | |
| WO | WO-2017024260 A1 * | 2/2017 | A61L 2/07 |

OTHER PUBLICATIONS

Chad Terhune, "Superbug outbreak: UCLA will test new scope-cleaning machine," LA Times, Jul. 22, 2015, http://www.latimes.com/business/la-fi-ucla-superbug-scope-testing-20150722-story.html, pp. 1-4.
CISA, "ERS Endoscope Reprocessing System," pp. 1-12.
PCT Notification of Transmittal of the International Search Report and the Written Opinion of the International Searching Authority, or the Declaration, International Application No. PCT/IB2019/061009, dated Mar. 19, 2020, 13 Pages.
Chinese First Office Action for CN201980084699 dated Oct. 8, 2022, 7 pages.
Chinese First Office Action in English for CN201980084699 dated Oct. 8, 2022, 9 pages.
Chinese First Search for CN201980084699 dated Sep. 26, 2022, 2 pages.

* cited by examiner

REPROCESSING CASE

CROSS-REFERENCE TO CO-PENDING APPLICATION

The present application claims the benefit under 35 U.S.C. § 119 of U.S. Provisional Patent Application No. 62/781,479, filed Dec. 18, 2018. The entire contents of this application is incorporated by reference herein in their entirety.

FIELD

The subject matter disclosed herein relates to systems for reprocessing of medical devices, particularly automated reprocessing of endoscopes.

BACKGROUND

Endoscopes are reusable medical devices. An endoscope should be reprocessed, i.e., decontaminated, between medical procedures in which it is used to avoid causing infection or illness in a subject. Endoscopes are difficult to decontaminate as has been documented in various news stories. See, e.g., Chad Terhune, "Superbug outbreak: UCLA will test new scope-cleaning machine," LA Times, Jul. 22, 2015, http://www.latimes.com/business/la-fi-ucla-superbug-scope-testing-20150722-story.html (last visited Oct. 30, 2017). Typically, endoscope reprocessing is performed by a disinfection procedure that includes at least the following steps: removing foreign material from the endoscope, cleaning the endoscope, and disinfecting the endoscope by, among other things, submerging it in a disinfectant capable of substantially killing microorganisms thereon, e.g., infection causing bacteria. One exemplary disinfectant is CIDEX® OPA Solution, manufactured and distributed by Advanced Sterilization Products ("ASP").

Endoscope reprocessing may be conducted by a healthcare worker, or with the assistance of machinery, such as an automated endoscope reprocessor ("AER"), e.g., ASP's EVOTECH® Endoscope Cleaner and Reprocessor. The initial steps of reprocessing should be conducted immediately or shortly after the endoscope has been used in a procedure, at the point of care, to remove bioburden from an endoscope before it can dry on the endoscope. The initial steps are typically performed by a nurse and include, among others, wiping down the endoscope, soaking it in a detergent solution, suctioning detergent through the endoscope, suctioning air through the endoscope, and flushing the channels. After the initial steps are performed the endoscope may be transported to a reprocessing area for further reprocessing, such as disinfection in an AER. Following disinfection the endoscope may be stored until its next use.

SUMMARY OF THE DISCLOSURE

Disclosed herein is a reprocessing case for an instrument, such as a medical device, particularly an endoscope, that may be used to assist in reprocessing the instrument in an automated reprocessor, such as an automated endoscope reprocessor. The reprocessing case may include a first segment with a first shell having a first barrel and a first faceplate connected to a first piston at least partially disposed within the first barrel. The first faceplate may include a first port disposed through the first faceplate and a first valve disposed in the first port. A first tube may be connected to the first valve.

The reprocessing case may also include a second segment with a second shell and a second faceplate. A hinge may connect the first shell to the second shell. The second shell may also include a second barrel. The second faceplate may thus comprise a connection to a second piston at least partially disposed within the second barrel. The second faceplate may also include a second port disposed through the second faceplate and a second valve disposed in the second port. A second tube may be connected to the second valve.

In a closed configuration, the first faceplate may contact the first shell and the first shell may contact the second shell. In a further closed configuration, the second faceplate may contact the second shell. In a disinfection configuration, the first faceplate may be displaced from the first shell such that the first faceplate does not contact the first shell. In a further disinfection configuration, the second faceplate may be displaced from the second shell such that the second faceplate does not contact the second shell. In at least one disinfection configuration, the first faceplate may be angled outwardly from the first shell. In a further or alternative disinfection configuration, the second faceplate may be angled outwardly from the second shell.

Additionally, the reprocessing case may include a manifold. The manifold may be at least partially disposed on the first faceplate. Alternatively or additionally, the manifold may be integrated in the first segment or the second segment of the case. The manifold may include at least one inlet port and at least four outlet ports, such as eight outlet ports.

The case may additionally include a drain. It may also include a spray nozzle attached to at least one of the output ports. The spray nozzle may comprise a rotary spray nozzle.

The case may be used to assist in reprocessing a medical device according to the following method and variations. First, the reprocessing case may be opened to an open configuration. Second, the medical device, such as an endoscope, may be placed into the reprocessing case. Third, the reprocessing case may be closed to a closed configuration. Fourth, the reprocessing case may be placed into a reprocessor. Fifth, the reprocessing case may be configured into a disinfection configuration. Sixth, the medical device may be disinfected, e.g., by spraying the endoscope with a disinfectant. Additionally, before spraying the endoscope with a disinfectant, the endoscope may be sprayed with a detergent. Seventh, the reprocessing case may be returned to the closed configuration.

In certain variations of the method, a fluid delivery assembly may be mated to a port of the reprocessing case. The port may comprise an inlet port of a manifold. The port may additionally or alternatively be disposed through a face of the reprocessing case. A lumen of the medical device may also be connected to the port. Accordingly, the disinfection step may include disinfecting the lumen of the medical device.

BRIEF DESCRIPTION OF THE DRAWINGS

While the specification concludes with claims, which particularly point out and distinctly claim the subject matter described herein, it is believed the subject matter will be better understood from the following description of certain examples taken in conjunction with the accompanying drawings, in which like reference numerals identify the same elements and in which:

MODES OF CARRYING OUT THE INVENTION

The following detailed description should be read with reference to the drawings, in which like elements in different drawings are identically numbered. The drawings, which are not necessarily to scale, depict selected embodiments and are not intended to limit the scope of the invention. The detailed description illustrates by way of example, not by way of limitation, the principles of the invention. This description will clearly enable one skilled in the art to make and use the invention, and describes several embodiments, adaptations, variations, alternatives and uses of the invention, including what is presently believed to be the best mode of carrying out the invention.

As used herein, the terms "about" or "approximately" for any numerical values or ranges indicate a suitable dimensional tolerance that allows the part or collection of components to function for its intended purpose as described herein. More specifically, "about" or "approximately" may refer to the range of values ±10% of the recited value, e.g. "about 90%" may refer to the range of values from 81% to 99%. In addition, as used herein, the terms "patient," "host," "user," and "subject" refer to any human or animal subject and are not intended to limit the systems or methods to human use, although use of the subject invention in a human patient represents a preferred embodiment.

Figure 1:
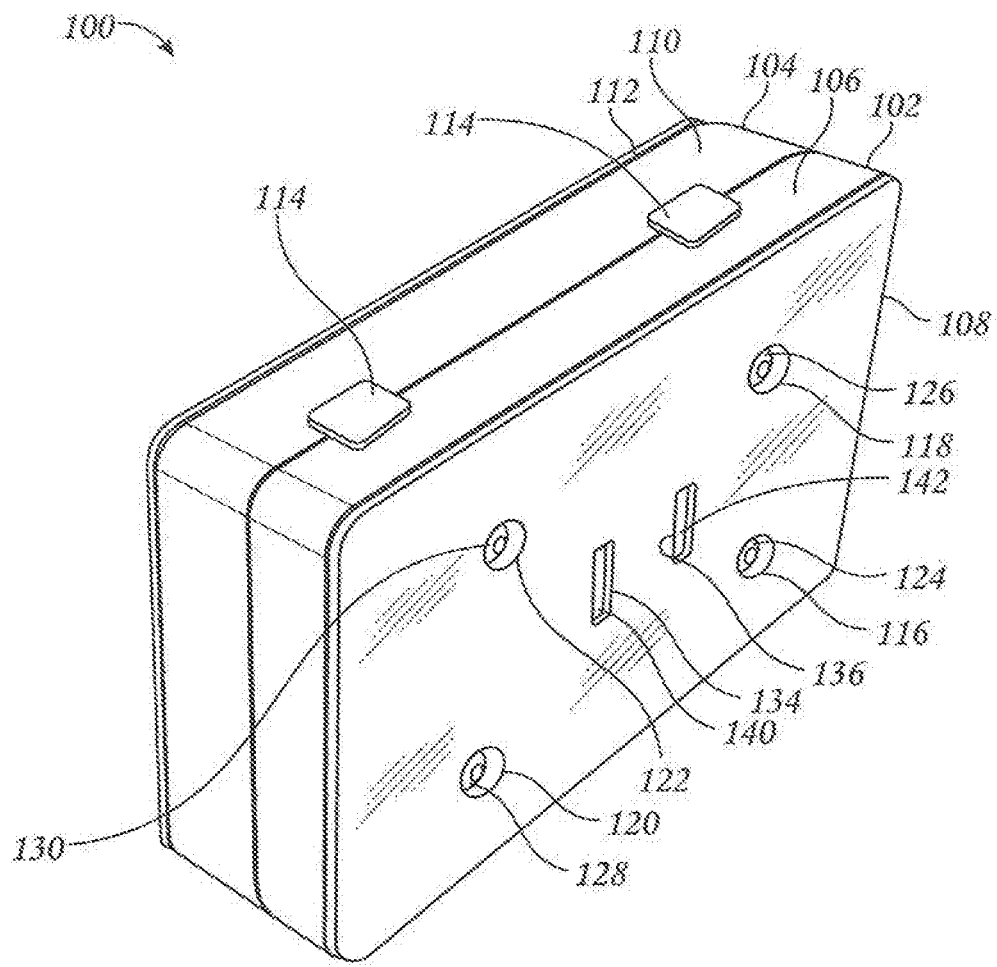
FIG. 1 depicts a reprocessing case in a closed configuration.

Described herein is a reprocessing case that may be used to facilitate disinfection of a medical device by an AER and subsequent storage of the medical device. Reprocessing case 100 is shown in a closed configuration in FIG. 1, a disinfection configuration in FIG. 2, and an open configuration in FIG. 3. Case 100 includes a first segment 102 and a second segment 104. First segment 102 includes a first shell 106 having a first faceplate 108. Second segment 104 includes a second shell 110 having a second faceplate 112. First shell 106 and second shell 110 may be connected by a hinge such that first segment 102 and second segment 104 may be rotated with respect to each other to change the configuration of the case from the closed configuration of FIG. 1 to the open configuration of FIG. 3. Segments 102 and 104 may be fabricated from any robust material, including metals and plastics, or a combination thereof. For example, the entirety of case 100 may be fabricated from one material or the other or a combination thereof. Stainless steel is an exemplary metal and polycarbonate is an exemplary plastic. As such, at least a portion of the case may be transparent, translucent, or opaque.

At least one clasp, such as two clasps 114 may be attached to either shell 106 or shell 110 and securable to the other shell such that the two shells may be secured to each other, similar to a brief case. A handle may additionally be disposed proximate to the claps on one of the two shell components. Accordingly, certain features of case 100 might be described as resembling a conventional briefcase.

Case 100 may additionally include various ports disposed through shells 106 and 110. For example, as shown in the figures, ports 116, 118, 120, and 122 are disposed through faceplate 108. The ports may respectively contain valves 124, 126, 128, and 130, which may be check valves, duckbill valves, umbrella valves, or X-fragm valves such as those manufactured by Minivalve, Inc., of Cleveland, Ohio. Although four ports and valves are shown, there may be any number of valves and ports as may be appropriate, e.g., between one port and ten ports, and between one valve and ten valves. These ports and valves may provide fluid-delivery assembly 132 (FIG. 4) of an AER access to the inside of case 100 during a disinfection procedure but restrict contaminants from entering the case during storage following the procedure.

Fluid delivery assembly 132 may be included as a subassembly of an AER, disposed in the reprocessing chamber. In addition to delivering liquids into case 100, assembly 132 may also function to change the configuration of the case from the closed configuration of FIG. 1 to the disinfection configuration of FIG. 2. For example, assembly 132 may be connected to a wall of the reprocessing chamber via a linear actuator such that linear actuation of assembly 132 moves assembly 132 away from the wall, toward case 100, and ultimately into contact with case 100.

Once extended from its home position and onto the case, the assembly 132 employs use of capture features to mate with connection features of case 100 for purposes of mechanical manipulation, e.g., movement of faceplate 108 away from shell 106. The capture features may be a spring loaded cam or mechanical fingers that mate to the connection figures press fit, friction fit, or snap fit. The connection features may include slots 134 and 136. A covering 140, e.g., a flexible sheet of material such as silicone, may be secured to an inner surface of faceplate 108 over slits 134 and 136 to allow mating of assembly 132 while providing a barrier to the exterior of faceplate 108 to restrict contaminants from entering the case through slots 134 and 136 during storage following the procedure. Alternatively, a second covering 142 may be included such that covering 140 covers slot 134 and covering 142 covers slot 136.

Once the capture features of assembly 132 are mated to the connection features of case 100, the assembly 132 is translated back toward the wall, i.e., its home position, which pulls face 108 away from shell 106, to transition case 100 from the closed configuration to the disinfection configuration. After the cycle is completed, the case wall is returned to the closed configuration and the capture features are relaxed to decouple assembly 132 from the connection features of case 100. The relaxation of the capture features may be linked to a separate movement of assembly 132 such as negative travel from the home position.

Figure 2:
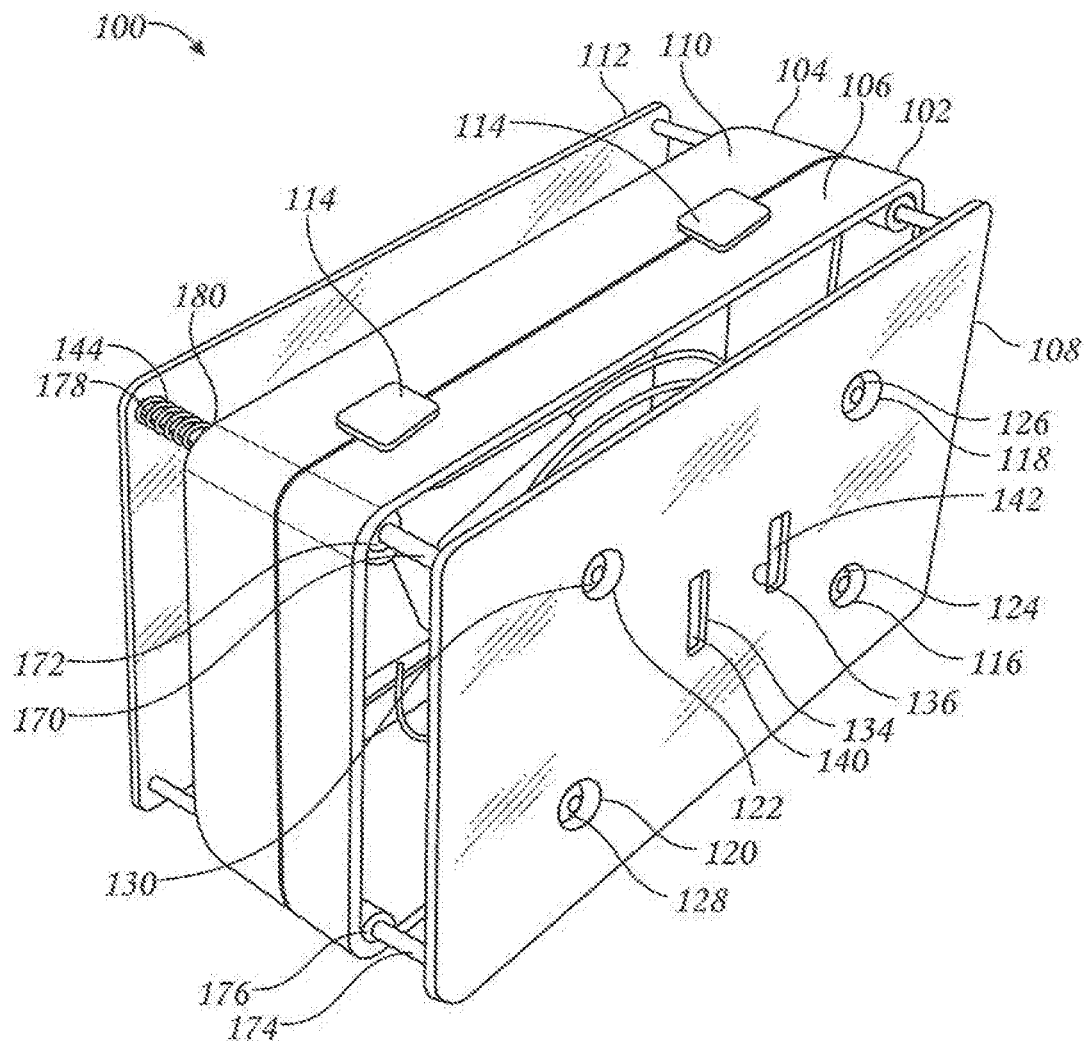
FIG. 2 depicts the reprocessing case of FIG. 1 in a first disinfection configuration.

FIG. 2 reflects case 100 in a disinfection configuration in which faceplate 108 is displaced from shell 106 and faceplate 112 is displaced from shell 110. As noted above, slots 134 and 136 may mate with features on assembly 132 such that assembly 132 may pull faceplate 108 away from shell 106 or push faceplate 108 back into contact with shell 106. Cylinders or pistons (e.g., 170, 174, 178) may be disposed in barrels (e.g., 172, 176, 180 (hidden)) of shell 106, and may help guide faceplate 108 between its two positions corresponding to the closed configuration and the disinfection configuration. Alternatively or additionally, faceplate 106 may be moved between its two positions without assistance from assembly 132. For example, a motor, such as a stepper motor, may be included within at least one of the barrels to translate its corresponding piston in and out of the barrel. The motor may be powered by battery power. Alternatively or additionally, springs (e.g., spring 144 may be included within any of the barrels or around any of the pistons to assist in returning case 100 to its closed configuration. A gasket or gasket material may be adhered to about the periphery of shell 106, faceplate 108, or both, such that shell 106 and faceplate 108 form a seal when case 100 is in a closed configuration. Similarly, gasket or gasket material may be adhered to about the periphery of shell 110, faceplate 112, or both, such that shell 110 and faceplate 112 form a seal when case 100 is in a closed configuration.

Figure 5:
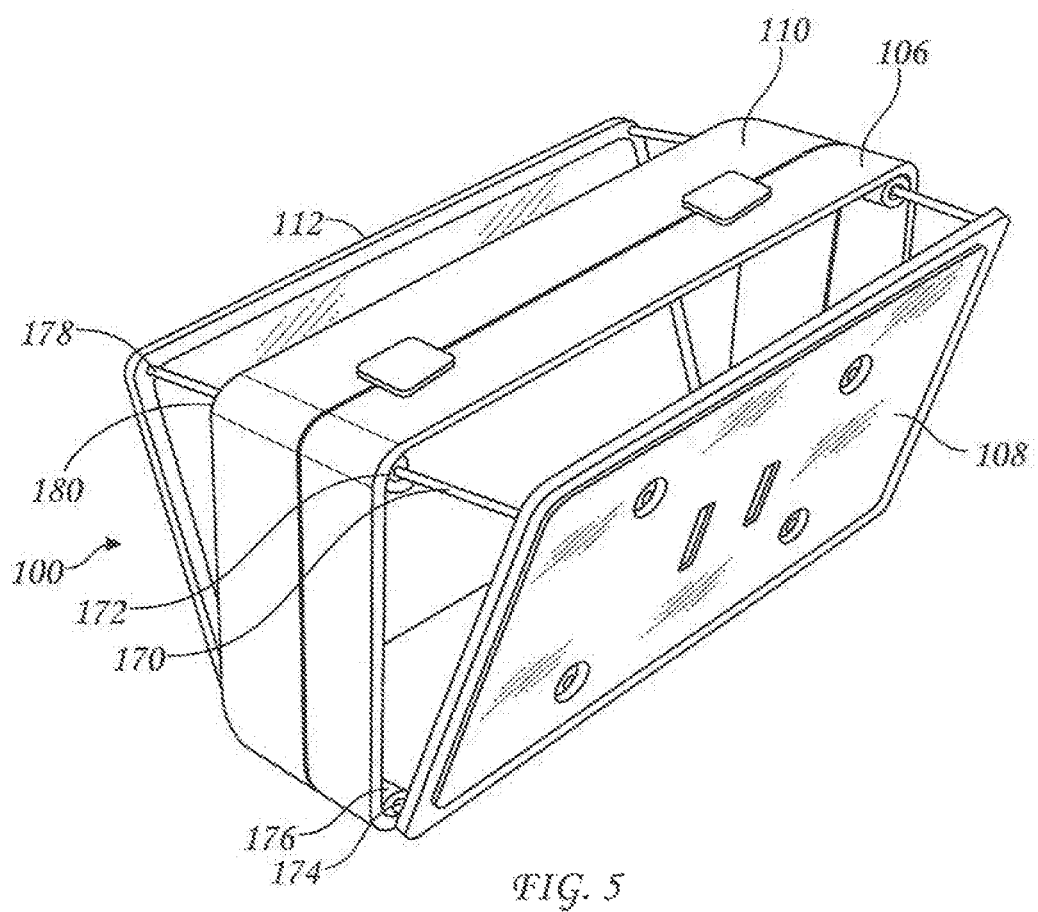
FIG. 5 depicts the reprocessing case of FIG. 1 in a second disinfection configuration.

An alternative disinfection configuration is reflected in FIG. 5. In this disinfection configuration faceplates 108 and 112 are angled outwardly from the corresponding shells 106 and 110. This may be accomplished by having some pistons having a longer stroke than some of the others. For example, in FIG. 5 piston 170 extends further outside of barrel 172 than piston 174 extends outside of barrel 176.

Figure 3:
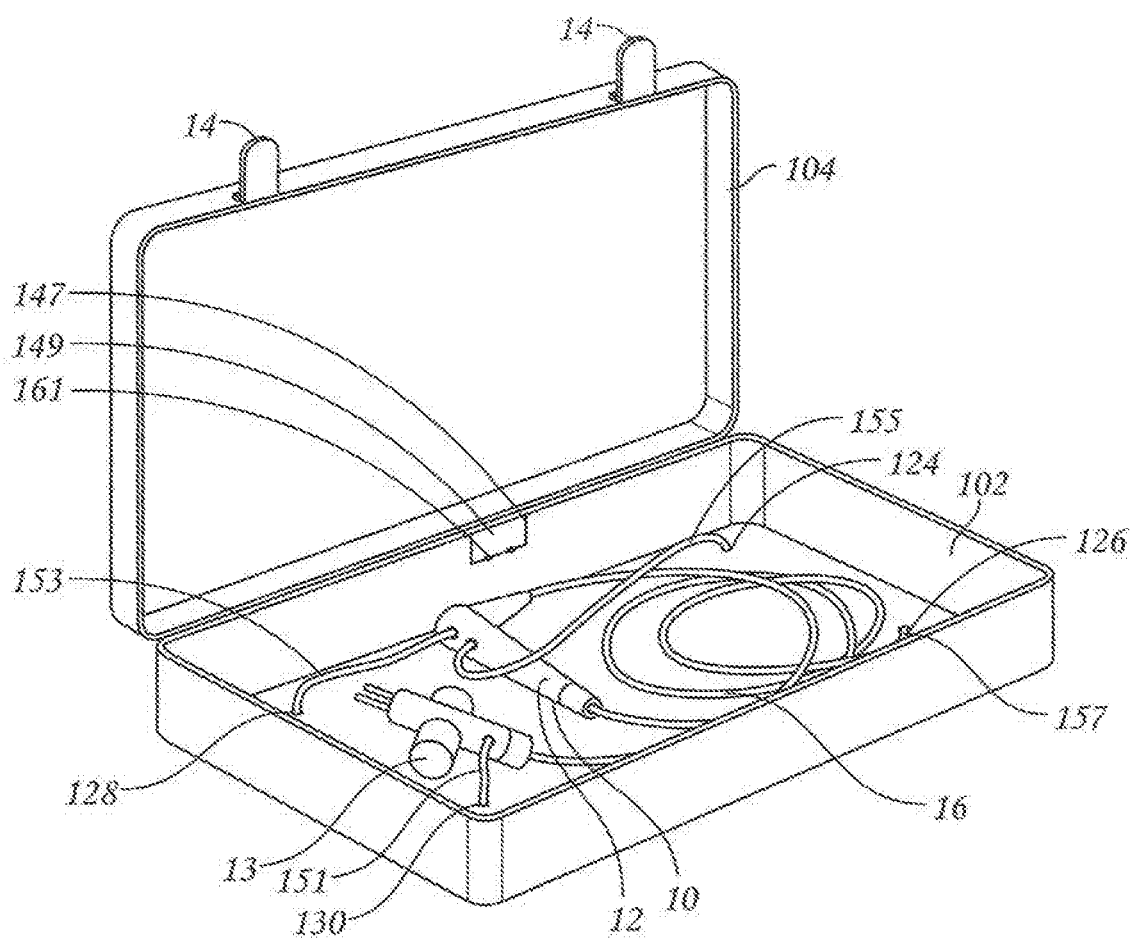
FIG. 3 depicts the reprocessing case of FIG. 1 in an open configuration.

FIG. 3 reflects case 100 in an open configuration in which segments 102 and 104 are disposed at 90 degrees or approximately 90 degrees relative to each other, in a configuration akin to an open configuration of a conventional brief case. In the open configuration, a medical device, such as endoscope 10, may be placed into the case before a disinfection procedure or removed from the case after the disinfection procedure. Additionally or alternatively, case 100 may include one or more tubes, e.g., as shown in FIG. 3, four tubes 151, 153, 155, and 157. One end of each tube may be respectively connected to valves 124, 126, 128, or 130, e.g., valve 128. The other end of these tubes may be respectively connected to a lumen of the endoscope, e.g., via ports on control body 12, ports on light connector 13, or via a distal end of insertion tube 16. Such connections assist in providing disinfectant, detergent, water, or air through lumens of the endoscope.

Case 100 may additionally include a drainage slot 149, which may be covered by door or cover 147 hinged about at least one hinge 161. As such, the drainage slot may be open during a disinfection procedure to allow liquids (e.g., disinfectant, detergent, water) to drain out of case 100, but closed to avoid contamination following the procedure during storage.

Figure 4:
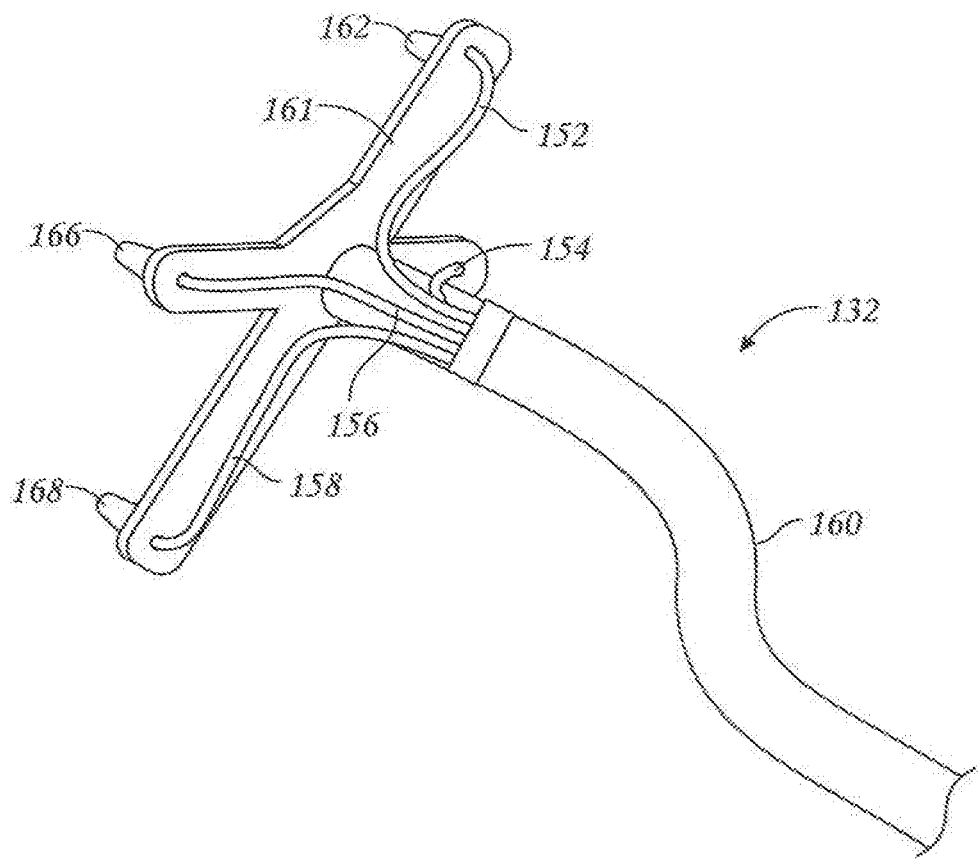
FIG. 4 depicts a first fluid delivery assembly configured to mate with the reprocessing case of FIG. 1.

A fluid delivery assembly 132 of an AER is shown in FIG. 4. Assembly 132 may be considered a manifold and includes at least one tube for conducting fluids, such as disinfectants, detergents, or water tubes from a corresponding supply to case 100. For example, as seen in FIG. 4, assembly 132 includes tubes 152, 154, 156, and 158. A proximal portion of each of these tubes may be connected to fluid supplies within the AER via a larger tube 160 that maintains each of tubes 152, 154, 156, and 158 contained therein for organization and to avoid stressing tubing connections during manipulation of assembly 132 during a disinfection procedure. The distal end of each tube 152, 154, 156, and 158 may be supported by a support fixture and mated to a corresponding nipple 162, 164 (hidden in FIG. 4), 166, and 168. These nipples are configured to be inserted into ports 116, 118, 120, and 122 and to open valves 124, 126, 128, and 130. As such fluids, (e.g., disinfectant, detergent, water, or air) may be delivered into case 100 via the tubes, nipples and valves.

Figure 6:
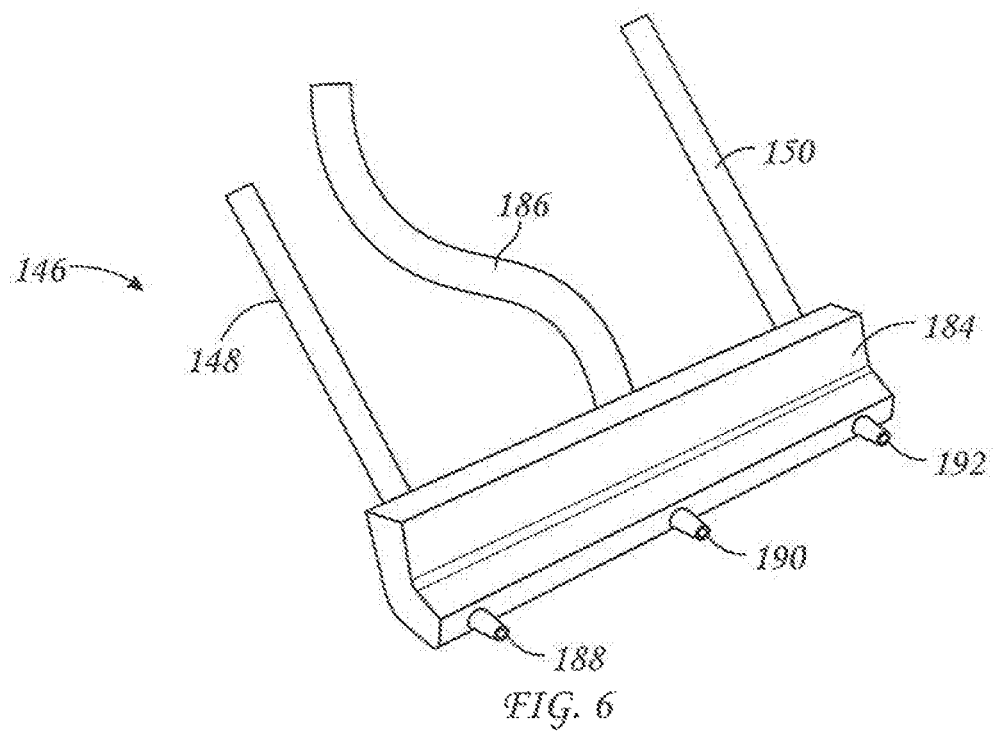
FIG. 6 depicts a second fluid delivery assembly that may be used with the reprocessing case of FIG. 1.

FIG. 6 shows a second fluid delivery assembly 146 that may be used in addition to or alternatively to assembly 132. Assembly 146 includes a manifold 184 supported by two support bars 148 and 150 and connected to a supply tube 186 connected to the AER's supplies of, e.g., air, water, disinfectant, and detergent. Manifold 184 also includes nipples 188, 190, and 192 from which the fluids may be expelled. Manifold 184 may be inserted into case 100, through the space between either faceplate 108 and shell 106 or faceplate 112 and shell 110 when case 100 is in a disinfection configuration. Thus, in embodiments that include both assemblies 132 and 146, assembly 132 may be used or at least primarily used to flow fluids through the endoscopes lumens whereas assembly 146 may be used or at least primarily used to spray the exterior of the endoscope with the fluids.

Figure 7:
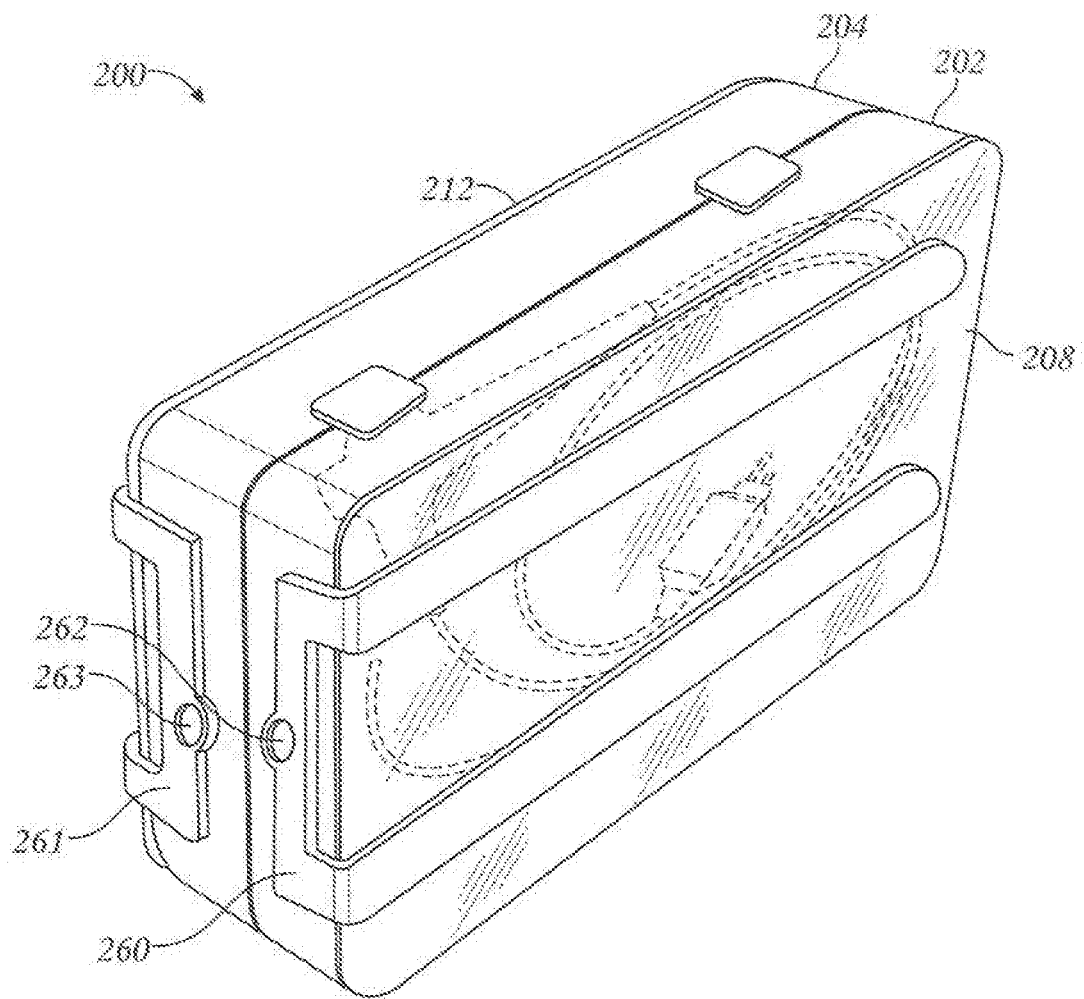
FIG. 7 depicts a reprocessing case including a manifold in a closed configuration.
Figure 8:
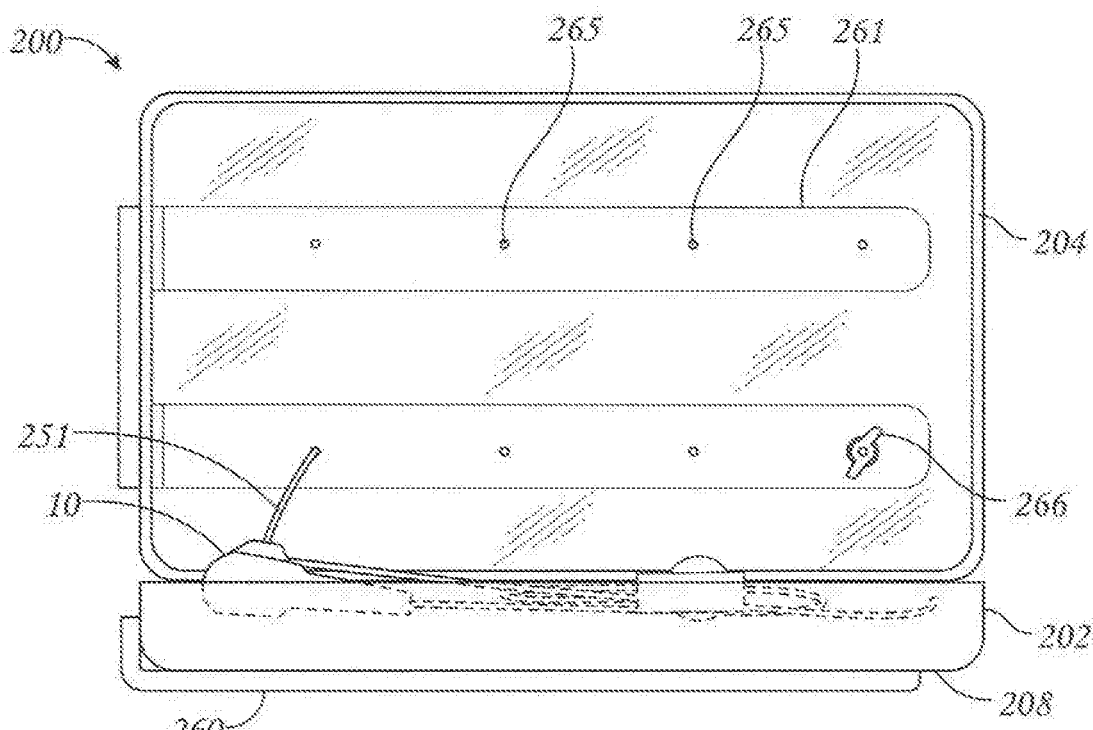
FIG. 8 depicts the reprocessing case of FIG. 7 in an open configuration.

FIGS. 7 and 8 reflect an alternative embodiment of a reprocessing case 200 in a closed configuration and open configuration, respectively. Case 200 includes a first segment 202 having a first faceplate 208 and a second segment 204 having a second faceplate 212. A first manifold 260 may be disposed upon segment 202, including faceplate 208. A second manifold 261 may be disposed upon segment 204, including faceplate 212. Manifold 260 may include an inlet port 262 and manifold 261 may include an inlet port 263. Manifolds 260 and 261 may also include various outlet ports. For example, as seen in FIG. 8, manifold 261 includes eight outlet ports 265. At least one tube 251 may also be included for connecting one of the outlet ports 265 to a lumen of endoscope 10. As such, fluid (e.g., air, disinfectant, water, or detergent) introduced into one or both of inlets 262 and 263 may be introduced into case 200 and endoscope lumens to disinfect the endoscope. In further embodiments, one or more of the outlet ports 265 may be outfitted with a spray nozzle 266, such as a rotary spray nozzle.

Figure 9:
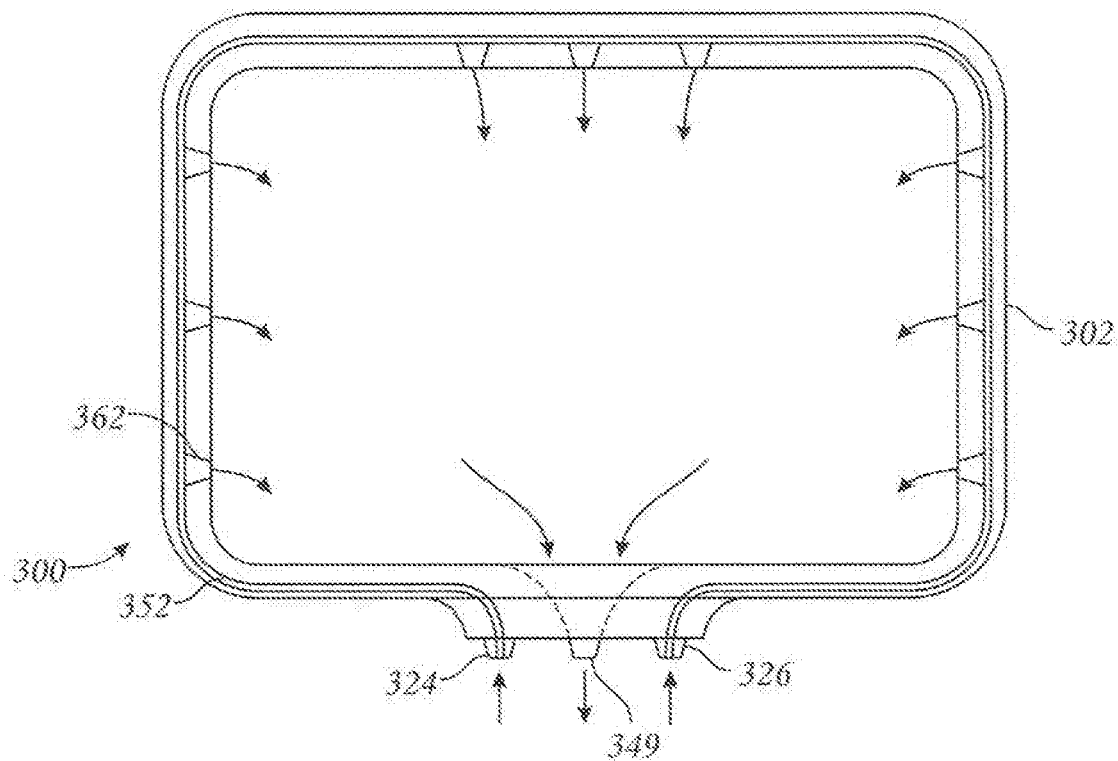
FIG. 9 depicts a cross-section of a reprocessing case that includes an integrated manifold.

Further flow mechanisms may be imparted to the reprocessing case, including to case 100 and case 200. One such flow mechanism is an integrated manifold, as reflected in FIG. 9. FIG. 9 shows one segment 302 of case 300, which segment 302 is analogous to segment 102 or 104 of case 100, or segment 202 or 204 of case 200. The manifold comprises a tube 352 in the body of segment 302 and wraps about nearly the entire contour of the body, beginning at first inlet or inlet port 324, such that the segment comprises the manifold. Additional inlets to tube 352 may be provided, such as second inlet 326. One or more output ports 362 may connect tube 352 to the inside of segment 302 such that fluid (e.g., disinfectant, water, detergent, or air) input through at least first inlet 324 may be expelled, preferably as a strong jet, out of ports 362 and into the inside of the case. Ideally, there are a greater number of output ports than inlets. Thus, there may be, e.g., one inlet port or two inlet ports, and four to twelve output ports. As shown in FIGS. 7 and 8, there the manifold includes one inlet port and eight outlet ports. Finally, a drain 349 may be included.

By virtue of the embodiments illustrated and described herein, Applicant has devised methods and variations thereof for disinfecting a medical device, particularly an endoscope, using an AER. For example, a reprocessing case, such as case 100 may be received in a closed configuration, such as that reflected in FIG. 1. The case may be opened to an open configuration, such as that reflected in FIG. 3. A medical device, e.g., an endoscope, may be placed into a portion of the case, such as segment 102. Lumens of the medical device may be connected via tubes (e.g., tubes 151, 153) to ports and valves through which fluids may be introduced into the case and the medical device (e.g., ports 116, 118 and valves 124, 126). The case may then be returned to a closed configuration. The case may then be placed into a disinfection chamber of an AER and secured therein. Alternatively, the case may be placed into a disinfection chamber of an AER before any of the foregoing steps.

After the case is disposed in the disinfection chamber of the AER in the closed configuration with the endoscope contained inside the case, a disinfection procedure may be commenced. The case may then be placed into a disinfection configuration, such as that shown in FIG. 2 or FIG. 5. That is, at least one faceplate (e.g., 108 or 112) of a component (e.g., 102 or 104) of the case may be displaced from a position in which it contacts a shell (e.g., 106 or 110) of that component to a position where it does not contact the shell. Such may be accomplished by pulling the faceplate away from the shell, e.g., by pulling or pushing the faceplate away from shell. The faceplate may be pulled away from the shell by first mating a fluid delivery assembly (e.g., 132) to mating features of the faceplate (e.g., slots 134 and 136). The fluid delivery assembly may then be moved away from the shell, pulling the faceplate with it. Pistons (e.g., 172, 178) that are connected to the faceplate and that are disposed within barrels (e.g., 172, 180) connected to the shell or integral with the shell may assist in guiding the faceplate. The faceplate may be returned to contact the shell either by being pushed by the fluid delivery assembly or under forces generated by a spring or springs (e.g., 178) disposed around one or more of the pistons that has been extended by the displacement. Further, a stepper motor or the like may be included within one or more of the barrels to push and pull the faceplate between the closed and disinfection configurations. While the case is in the disinfection configuration, various fluids (e.g., detergent, disinfectant, water, and air) may be introduced into the case and into the medical device to clean, disinfect, and dry them. Such fluids may be introduced into the case via the space between the faceplate and the shell such as by fluid delivery assembly 146, or through ports disposed through the faceplate, such as by fluid delivery assembly 132. Subsequently, case 100 may be returned to the closed configuration. The reprocessing procedure may be ended and the case removed from the AER. The case may then be stored with the disinfected medical device therein.

Any of the examples or embodiments described herein may include various other features in addition to or in lieu of those described above. The teachings, expressions, embodiments, examples, etc., described herein should not be viewed in isolation relative to each other. Various suitable ways in which the teachings herein may be combined should be clear to those skilled in the art in view of the teachings herein.

Having shown and described exemplary embodiments of the subject matter contained herein, further adaptations of the methods and systems described herein may be accomplished by appropriate modifications without departing from the scope of the claims. In addition, where methods and steps described above indicate certain events occurring in certain order, it is intended that certain steps do not have to be performed in the order described but in any order as long as the steps allow the embodiments to function for their intended purposes. Therefore, to the extent there are variations of the invention, which are within the spirit of the disclosure or equivalent to the inventions found in the claims, it is the intent that this patent will cover those variations as well. Some such modifications should be apparent to those skilled in the art. For instance, the examples, embodiments, geometrics, materials, dimensions, ratios, steps, and the like discussed above are illustrative. Accordingly, the claims should not be limited to the specific details of structure and operation set forth in the written description and drawings.

We claim:

1. A reprocessing case, comprising:
   a first segment including,
      a first shell having a first barrel,
      a first faceplate connected to a first piston at least partially disposed within the first barrel,
      a first port disposed through the first faceplate, and
      a first valve disposed through the first port;
   a second segment including a second shell and a second faceplate;
   a hinge connecting the first shell to the second shell, in which the first faceplate contacts the first shell to define a closed configuration of the reprocessing case; and
   a fluid delivery assembly connected to the first faceplate such that, in the closed configuration, the first faceplate is moveable away from the first shell by the fluid delivery assembly in a first direction and is not moveable toward the second shell by the fluid delivery assembly in a second direction opposite the first direction.

2. The reprocessing case of claim 1, wherein the first faceplate is angled outwardly from the first shell.

3. The reprocessing case of claim 1, further including a first tube connected to the first valve.

4. The reprocessing case of claim 3, wherein the second shell further includes a second barrel and the second faceplate comprises a connection to a second piston at least partially disposed within the second barrel.

5. The reprocessing case of claim 4, wherein the second faceplate includes:
   a second port disposed through the second faceplate; and
   a second valve disposed in the second port.

6. The reprocessing case of claim 5, wherein the second faceplate contacts the second shell.

7. The reprocessing case of claim 5, wherein the second faceplate is displaced from and does not contact the second shell.

8. The reprocessing case of claim 7, wherein the second faceplate is angled outwardly from the second shell.

9. The reprocessing case of claim 5, further including a second tube connected to the second valve.

10. The reprocessing case of claim 1, further comprising a manifold.

11. The reprocessing case of claim 10, wherein the manifold is at least partially disposed on the first faceplate.

12. The reprocessing case of claim 10, wherein the manifold is integrated in the first segment of the case.

13. The reprocessing case of claim 10, wherein the manifold includes at least one inlet port and at least four outlet ports.

14. The reprocessing case of claim 13, wherein the manifold includes one inlet port and eight outlet ports.

15. The reprocessing case of claim 13, further including a drain.

16. The reprocessing case of claim 13, further including a spray nozzle attached to at least one of the outlet ports.

17. The reprocessing case of claim 16, wherein the spray nozzle comprises a rotary spray nozzle.

* * * * *